US007722877B2

(12) United States Patent
Schaap et al.

(10) Patent No.: US 7,722,877 B2
(45) Date of Patent: May 25, 2010

(54) COCCIDIOSIS VACCINES

(75) Inventors: Theodorus Cornelis Schaap, 's-Hertogenbosch (NL); Catharina Maria Kuiper, 's-Hertogenbosch (NL); Arnoldus Nicolaas Vermeulen, Cuyk (NL)

(73) Assignee: Intervet International B.V., Boxmeer (NL)

( * ) Notice: Subject to any disclaimer, the term of this patent is extended or adjusted under 35 U.S.C. 154(b) by 467 days.

(21) Appl. No.: 11/594,367

(22) Filed: Nov. 7, 2006

(65) Prior Publication Data

US 2007/0166334 A1 Jul. 19, 2007

Related U.S. Application Data

(62) Division of application No. 10/723,123, filed on Nov. 26, 2003, now Pat. No. 7,150,873, which is a division of application No. 09/749,233, filed on Dec. 27, 2000, now Pat. No. 6,680,061, which is a division of application No. 09/411,578, filed on Oct. 4, 1999, now Pat. No. 6,203,801.

(30) Foreign Application Priority Data

Oct. 7, 1998 (EP) .................................. 98203384
Oct. 16, 1998 (EP) .................................. 98203457

(51) Int. Cl.
*A61K 39/00* (2006.01)
*A61K 39/012* (2006.01)
*C07H 21/04* (2006.01)
*C12P 21/06* (2006.01)

(52) U.S. Cl. ............... 424/184.1; 424/269.1; 424/267.1; 424/265.1; 435/69.1; 435/69.5; 435/320.1; 514/44; 536/23.5; 536/23.7

(58) Field of Classification Search ....................... None
See application file for complete search history.

(56) References Cited

U.S. PATENT DOCUMENTS

| 4,981,684 | A | 1/1991 | MacKenzie et al. |
| 5,597,807 | A | 1/1997 | Estrada et al. |
| 5,670,362 | A | 9/1997 | Vermeulen et al. |
| 5,780,289 | A | 7/1998 | Vermeulen et al. |
| 5,789,233 | A | 8/1998 | Vermeulen et al. |
| 5,792,644 | A | 8/1998 | Vermeulen et al. |
| 5,925,347 | A | 7/1999 | Vermeulen et al. |
| 6,203,801 | B1 | 3/2001 | Schaap et al. |
| 6,680,061 | B1 | 1/2004 | Schaap et al. |
| 7,150,873 | B2 | 12/2006 | Schaap et al. |
| 2002/0006408 | A1 | 1/2002 | Vermeulen et al. |

FOREIGN PATENT DOCUMENTS

| EP | 0 135 712 | 4/1985 |
| EP | 0 231 537 | 8/1987 |
| EP | 0 324 648 | 7/1989 |
| EP | 0 337 589 | 10/1989 |
| EP | 0 382 531 | 8/1990 |
| EP | 0 439 056 | 7/1991 |
| EP | 838 522 | 4/1998 |
| EP | 0 872 486 | 10/1998 |
| NZ | 330158 | 7/1998 |

OTHER PUBLICATIONS

Gurnett, A. et al., "A family of glycolipid linked in Eimeria tenella," Molecular and Biochemical Parasitology, 1990 41:177-186.
Houghten, R.A. et al., "Relative Importance of Position and Individual . . . " Vaccines 86, Fred Brown, ed., Cold Spring Harbor Laboratory, 1986 pp. 21-25.
Burgess, W. et al., "Possible Dissociation of the Heparin-binding and Mitogenic Activities of Heparin-binding (Acidic Fibroblast) . . . " J. of Cell Biology, 1990, 111:2129-2138.
Lazar, E. et al., "Transforming Growth Factor a: Mutuation of Aspartic Acid 47 and Leucine 48 Results . . . " Molecular and Cellular Biology 8:1247-1252 (Mar. 1988).
Prosecution History for U.S. Appl. No. 09/056,806, filed Apr. 8, 1998, Vermeulen et al.
Danforth, H.D. et al., "Genetically Engineered Antigen Confers Partial Protection Against Avian Coccidial Parasites," Poultry Science, vol. 68, 1989, pp. 1643-1652.
Karkhanis, Y.D. et al., "Purification and Characterization of a Protective Antigen from Eimeria Tenella," Infection and Immunity, vol. 59, No. 3, Mar. 1991, pp. 983-989.
Purdy, D. et al., "Cloning, Nucleotide Sequence and Characterization of a Gene Encoding Superoxide Dismutase from Campylobacter Jejuni and Campylobacter Coli," Microbiology, vol. 140, May 1994, pp. 1203-1208.
Jenkins, M.C. et al., "cDNA Encoding an Immunogenic Region of a 22 kilodalton Surface Protein of Eimeria Acervulina Sporozoites," Molecular and Biochemical Parasitology, vol. 32, 1989, pp. 153-162.
Ranie, J. et al., "Cloning of the Triosephosphate Isomerase Gene of Plasmodium Falciparum and Expression in *Escherichia Coli*," Molecular and Biochemical Parasitology, vol. 61, No. 2, 1993, pp. 159-169.
Deshazer, D. et al., "Characterization of the GEne Encoding Superoxide Dismutase of Bordetella Pertussis and Construction of a SOD-deficient Mutuant," Gene, vol. 142, 1994, pp. 85-89.
Lim, Yoo-Shick et al., "The Thiol-specific Antioxidant Protein from Human Brain: Gene Cloning and Analysis of Conserved Cysteine Regions," Gen, vol. 140, 1994, pp. 279-284.
Becuwe, P. et al., "Characterization of Iron-dependent Endogenous Superoxide Dismutase of Plasmodium Falciparum," Molecular and Biochemical Parasitology, vol. 76, 1996, pp. 125-134.
Bowie et al., Science, vol. 247, 1990, pp. 1306-1308.

*Primary Examiner*—Robert Mondesi
*Assistant Examiner*—Padma Baskar
(74) *Attorney, Agent, or Firm*—William M. Blackstone; Aaron L. Schwartz

(57) ABSTRACT

The present invention relates to hydrophilic *Eimeria* polypeptides, DNA-fragments encoding those peptides, recombinant DNA molecules comprising such DNA-fragments, live recombinant carriers comprising such DNA-fragments or recombinant DNA molecules and host cells comprising such DNA-fragments, recombinant DNA molecules or live recombinant carriers. Furthermore, the invention relates to antibodies against the polypeptides and to coccidiosis vaccines based upon said polypeptides. The invention also relates to methods for the preparation of such antibodies and vaccines, and to methods for the detection of *Eimeria* parasites and antibodies against *Eimeria* parasites.

6 Claims, No Drawings

US 7,722,877 B2

SEQUENCE LISTING

<160> NUMBER OF SEQ ID NOS: 43

<210> SEQ ID NO 1
<211> LENGTH: 214
<212> TYPE: PRT
<213> ORGANISM: Eimeria tenella

<400> SEQUENCE: 1

```
Met Pro Phe Glu Leu Pro Pro Leu Pro Tyr Pro Met Asp Ala Leu Glu
1               5                   10                  15

Pro Tyr Ile Ser Lys Glu Thr Leu Glu Tyr His Tyr Gly Lys His His
            20                  25                  30

Ala Ala Tyr Val Asn Asn Leu Asn Arg Leu Val Glu Gly Lys Pro Glu
        35                  40                  45

Ala Ser Lys Ser Leu Glu Glu Ile Ile Lys Thr Ser Ser Gly Ser Val
    50                  55                  60

Leu Asn Asn Ala Gly Gln Ala Trp Asn His Thr Phe Tyr Trp Lys Ser
65                  70                  75                  80

Met Arg Pro Ala Ser Ala Gly Gly Pro Pro Gly Ala Pro Gly Gly Gly
                85                  90                  95

Pro Pro Gly Ala Pro Gly Ala Pro Leu Arg Glu Glu Leu Glu Ser Ala
            100                 105                 110

Phe Gly Gly Val Glu Lys Phe Arg Glu Ala Phe Ala Ala Ala Ala
        115                 120                 125

Ala His Phe Gly Ser Gly Trp Ala Trp Leu Cys Phe Cys Lys Lys Ser
    130                 135                 140

Arg Ser Leu Phe Leu Leu Gln Thr His Asp Gly Ala Thr Pro Phe Arg
145                 150                 155                 160
```

```
Asp Asn Pro Asn Cys Ala Pro Leu Leu Thr Cys Asp Leu Trp Glu His
            165                 170                 175

Ala Tyr Tyr Ile Asp Arg Arg Asn Asp Arg Lys Ser Tyr Leu Asp Ala
            180                 185                 190

Trp Trp Ser Val Val Asn Trp Asp Phe Ala Asn Glu Asn Leu Lys Lys
            195                 200                 205

Ala Met Gln Gly Ser Asp
        210

<210> SEQ ID NO 2
<211> LENGTH: 13
<212> TYPE: PRT
<213> ORGANISM: Eimeria tenella

<400> SEQUENCE: 2

Leu Gly Pro Leu Ala Leu Pro Leu Leu Ala Asp Val Arg
1               5                   10

<210> SEQ ID NO 3
<211> LENGTH: 223
<212> TYPE: PRT
<213> ORGANISM: Eimeria tenella

<400> SEQUENCE: 3

Met Pro Leu Asn Leu Gly Asp Ser Phe Pro Asp Phe Gln Ala Glu Ala
1               5                   10                  15

Leu Gly Ala Glu His Phe Arg Leu His Glu Tyr Leu Gly Asp Ser Trp
            20                  25                  30

Gly Val Met Phe Ser His Pro Asn Asp Phe Thr Pro Val Cys Thr Thr
        35                  40                  45

Glu Leu Ala Glu Ala Val Lys Leu Gln Asp Ser Phe Thr Lys Lys Asn
 50                 55                  60

Cys Lys Leu Val Gly Phe Ser Cys Asn Asp Leu Gln Ser His Arg Glu
65                  70                  75                  80

Trp Ala Lys Asp Ile Met Ala Tyr Ala Gly Arg Ser Gly Asn Leu Pro
            85                  90                  95

Phe Pro Leu Val Cys Asp Pro Asn Arg Glu Leu Ala Ala Ser Leu Gly
            100                 105                 110

Ile Met Asp Pro Ala Glu Lys Asp Lys Lys Gly Leu Pro Leu Thr Cys
            115                 120                 125

Arg Cys Val Phe Phe Ile Ser Pro Glu Lys Lys Leu Ala Ala Ser Ile
        130                 135                 140

Leu Tyr Pro Ala Thr Thr Gly Arg Asn Phe Ala Glu Ile Leu Arg Val
145                 150                 155                 160

Leu Asp Ser Leu Gln Leu Thr Ala Lys Phe Pro Val Ala Thr Pro Val
            165                 170                 175

Asp Trp Thr Ala Gly Ala Lys Cys Cys Val Val Pro Asn Leu Ala Ala
            180                 185                 190

Glu Glu Ala Gln Arg Leu Leu Pro Lys Gly His Glu Ala Leu Gln Leu
            195                 200                 205

Pro Ser Gly Lys Pro Tyr Leu Arg Leu Thr Pro Asp Pro Arg Gly
        210                 215                 220

<210> SEQ ID NO 4
<211> LENGTH: 15
<212> TYPE: PRT
<213> ORGANISM: Eimeria tenella
```

-continued

```
<400> SEQUENCE: 4

Met Ser Pro Ser Pro Ala Gly Val Ala Glu Tyr Leu Ala Ser Leu
1               5                   10                  15

<210> SEQ ID NO 5
<211> LENGTH: 16
<212> TYPE: PRT
<213> ORGANISM: Eimeria tenella

<400> SEQUENCE: 5

Asn His Ala Glu Phe Asp Pro Ser Gln Thr Glu Val Val Val Phe Pro
1               5                   10                  15

<210> SEQ ID NO 6
<211> LENGTH: 20
<212> TYPE: PRT
<213> ORGANISM: Eimeria tenella

<400> SEQUENCE: 6

Val Asp Ser Phe Thr Pro Ser Val Gly Cys Val Phe Ala Gly Met Pro
1               5                   10                  15

Ala Asp Phe Arg
            20

<210> SEQ ID NO 7
<211> LENGTH: 17
<212> TYPE: DNA
<213> ORGANISM: Artificial
<220> FEATURE:
<223> OTHER INFORMATION: PCR/Cloning primer

<400> SEQUENCE: 7
gtaaattggg acttcgc                                                  17

<210> SEQ ID NO 8
<211> LENGTH: 17
<212> TYPE: DNA
<213> ORGANISM: Artificial
<220> FEATURE:
<223> OTHER INFORMATION: PCR/Cloning primer

<400> SEQUENCE: 8
gtaaactggg acttcgc                                                  17

<210> SEQ ID NO 9
<211> LENGTH: 17
<212> TYPE: DNA
<213> ORGANISM: Artificial
<220> FEATURE:
<223> OTHER INFORMATION: PCR/Cloning primer

<400> SEQUENCE: 9
gtaaattggg acttcgc                                                  17

<210> SEQ ID NO 10
<211> LENGTH: 17
<212> TYPE: DNA
<213> ORGANISM: Artificial
<220> FEATURE:
<223> OTHER INFORMATION: PCR/Cloning primer

<400> SEQUENCE: 10
gtaaactggg acttcgc                                                  17
```

```
<210> SEQ ID NO 11
<211> LENGTH: 17
<212> TYPE: DNA
<213> ORGANISM: Artificial
<220> FEATURE:
<223> OTHER INFORMATION: PCR/Cloning primer

<400> SEQUENCE: 11
gttaattggg acttcgc                                                    17

<210> SEQ ID NO 12
<211> LENGTH: 17
<212> TYPE: DNA
<213> ORGANISM: Artificial
<220> FEATURE:
<223> OTHER INFORMATION: PCR/Cloning primer

<400> SEQUENCE: 12
gttaactggg acttcgc                                                    17

<210> SEQ ID NO 13
<211> LENGTH: 17
<212> TYPE: DNA
<213> ORGANISM: Artificial
<220> FEATURE:
<223> OTHER INFORMATION: PCR/Cloning primer

<400> SEQUENCE: 13
gttaattggg acttcgc                                                    17

<210> SEQ ID NO 14
<211> LENGTH: 17
<212> TYPE: DNA
<213> ORGANISM: Artificial
<220> FEATURE:
<223> OTHER INFORMATION: PCR/Cloning primer

<400> SEQUENCE: 14
gttaactggg acttcgc                                                    17

<210> SEQ ID NO 15
<211> LENGTH: 17
<212> TYPE: DNA
<213> ORGANISM: Artificial
<220> FEATURE:
<223> OTHER INFORMATION: PCR/Cloning primer

<400> SEQUENCE: 15
gtgaattggg actttgc                                                    17

<210> SEQ ID NO 16
<211> LENGTH: 17
<212> TYPE: DNA
<213> ORGANISM: Artificial
<220> FEATURE:
<223> OTHER INFORMATION: PCR/Cloning primer

<400> SEQUENCE: 16
gtgaactggg actttgc                                                    17

<210> SEQ ID NO 17
<211> LENGTH: 17
<212> TYPE: DNA
<213> ORGANISM: Artificial
<220> FEATURE:
<223> OTHER INFORMATION: PCR/Cloning primer
```

<400> SEQUENCE: 17
gtgaattggg actttgc                                                          17

<210> SEQ ID NO 18
<211> LENGTH: 17
<212> TYPE: DNA
<213> ORGANISM: Artificial
<220> FEATURE:
<223> OTHER INFORMATION: PCR/Cloning primer

<400> SEQUENCE: 18
gtgaactggg actttgc                                                          17

<210> SEQ ID NO 19
<211> LENGTH: 17
<212> TYPE: DNA
<213> ORGANISM: Artificial
<220> FEATURE:
<223> OTHER INFORMATION: PCR/Cloning primer

<400> SEQUENCE: 19
gtcaattggg actttgc                                                          17

<210> SEQ ID NO 20
<211> LENGTH: 17
<212> TYPE: DNA
<213> ORGANISM: Artificial
<220> FEATURE:
<223> OTHER INFORMATION: PCR/Cloning primer

<400> SEQUENCE: 20
gtcaactggg actttgc                                                          17

<210> SEQ ID NO 21
<211> LENGTH: 17
<212> TYPE: DNA
<213> ORGANISM: Artificial
<220> FEATURE:
<223> OTHER INFORMATION: PCR/Cloning primer

<400> SEQUENCE: 21
gtcaattggg actttgc                                                          17

<210> SEQ ID NO 22
<211> LENGTH: 17
<212> TYPE: DNA
<213> ORGANISM: Artificial
<220> FEATURE:
<223> OTHER INFORMATION: PCR/Cloning primer

<400> SEQUENCE: 22
gtcaactggg actttgc                                                          17

<210> SEQ ID NO 23
<211> LENGTH: 17
<212> TYPE: DNA
<213> ORGANISM: Artificial
<220> FEATURE:
<223> OTHER INFORMATION: PCR/Cloning primer

<400> SEQUENCE: 23
gtaaattggg atttcgc                                                          17

```
<210> SEQ ID NO 24
<211> LENGTH: 17
<212> TYPE: DNA
<213> ORGANISM: Artificial
<220> FEATURE:
<223> OTHER INFORMATION: PCR/Cloning primer

<400> SEQUENCE: 24
gtaaactggg atttcgc                                                 17

<210> SEQ ID NO 25
<211> LENGTH: 17
<212> TYPE: DNA
<213> ORGANISM: Artificial
<220> FEATURE:
<223> OTHER INFORMATION: PCR/Cloning primer

<400> SEQUENCE: 25
gtaaattggg atttcgc                                                 17

<210> SEQ ID NO 26
<211> LENGTH: 17
<212> TYPE: DNA
<213> ORGANISM: Artificial
<220> FEATURE:
<223> OTHER INFORMATION: PCR/Cloning primer

<400> SEQUENCE: 26
gtaaactggg atttcgc                                                 17

<210> SEQ ID NO 27
<211> LENGTH: 17
<212> TYPE: DNA
<213> ORGANISM: Artificial
<220> FEATURE:
<223> OTHER INFORMATION: PCR/Cloning primer

<400> SEQUENCE: 27
gttaattggg atttcgc                                                 17

<210> SEQ ID NO 28
<211> LENGTH: 17
<212> TYPE: DNA
<213> ORGANISM: Artificial
<220> FEATURE:
<223> OTHER INFORMATION: PCR/Cloning primer

<400> SEQUENCE: 28
gttaactggg atttcgc                                                 17

<210> SEQ ID NO 29
<211> LENGTH: 17
<212> TYPE: DNA
<213> ORGANISM: Artificial
<220> FEATURE:
<223> OTHER INFORMATION: PCR/Cloning primer

<400> SEQUENCE: 29
gttaattggg atttcgc                                                 17

<210> SEQ ID NO 30
<211> LENGTH: 17
<212> TYPE: DNA
<213> ORGANISM: Artificial
<220> FEATURE:
<223> OTHER INFORMATION: PCR/Cloning primer
```

```
<400> SEQUENCE: 30
gttaactggg attttcgc                                                17

<210> SEQ ID NO 31
<211> LENGTH: 17
<212> TYPE: DNA
<213> ORGANISM: Artificial
<220> FEATURE:
<223> OTHER INFORMATION: PCR/Cloning primer

<400> SEQUENCE: 31
gtgaattggg attttgc                                                 17

<210> SEQ ID NO 32
<211> LENGTH: 17
<212> TYPE: DNA
<213> ORGANISM: Artificial
<220> FEATURE:
<223> OTHER INFORMATION: PCR/Cloning primer

<400> SEQUENCE: 32
gtgaactggg attttgc                                                 17

<210> SEQ ID NO 33
<211> LENGTH: 17
<212> TYPE: DNA
<213> ORGANISM: Artificial
<220> FEATURE:
<223> OTHER INFORMATION: PCR/Cloning primer

<400> SEQUENCE: 33
gtgaattggg attttgc                                                 17

<210> SEQ ID NO 34
<211> LENGTH: 17
<212> TYPE: DNA
<213> ORGANISM: Artificial
<220> FEATURE:
<223> OTHER INFORMATION: PCR/Cloning primer

<400> SEQUENCE: 34
gtgaactggg attttgc                                                 17

<210> SEQ ID NO 35
<211> LENGTH: 17
<212> TYPE: DNA
<213> ORGANISM: Artificial
<220> FEATURE:
<223> OTHER INFORMATION: PCR/Cloning primer

<400> SEQUENCE: 35
gtcaattggg attttgc                                                 17

<210> SEQ ID NO 36
<211> LENGTH: 17
<212> TYPE: DNA
<213> ORGANISM: Artificial
<220> FEATURE:
<223> OTHER INFORMATION: PCR/Cloning primer

<400> SEQUENCE: 36
gtcaactggg attttgc                                                 17
```

```
<210> SEQ ID NO 37
<211> LENGTH: 17
<212> TYPE: DNA
<213> ORGANISM: Artificial
<220> FEATURE:
<223> OTHER INFORMATION: PCR/Cloning primer

<400> SEQUENCE: 37
gtcaattggg attttgc                                                    17

<210> SEQ ID NO 38
<211> LENGTH: 17
<212> TYPE: DNA
<213> ORGANISM: Artificial
<220> FEATURE:
<223> OTHER INFORMATION: PCR/Cloning primer

<400> SEQUENCE: 38
gtcaactggg attttgc                                                    17

<210> SEQ ID NO 39
<211> LENGTH: 719
<212> TYPE: DNA
<213> ORGANISM: Eimeria tenella
<220> FEATURE:
<221> NAME/KEY: CDS
<222> LOCATION: (1)..(645)

<400> SEQUENCE: 39
```

| | | | | | | | | | | | | | | | | |
|---|---|---|---|---|---|---|---|---|---|---|---|---|---|---|---|---|
| atg | ccg | ttc | gaa | ctc | ccc | ccg | ctg | ccg | tac | ccc | atg | gac | gcc | ctc | gag | 48 |
| Met | Pro | Phe | Glu | Leu | Pro | Pro | Leu | Pro | Tyr | Pro | Met | Asp | Ala | Leu | Glu | |
| 1 | | | | 5 | | | | | 10 | | | | | 15 | | |
| ccg | tac | atc | agc | aaa | gag | act | ctc | gag | tac | cac | tat | ggg | aag | cac | cac | 96 |
| Pro | Tyr | Ile | Ser | Lys | Glu | Thr | Leu | Glu | Tyr | His | Tyr | Gly | Lys | His | His | |
| | | | 20 | | | | | 25 | | | | | 30 | | | |
| gcg | gct | tac | gtg | aac | aac | ttg | aac | aga | ctc | gtc | gag | ggg | aag | ccg | gag | 144 |
| Ala | Ala | Tyr | Val | Asn | Asn | Leu | Asn | Arg | Leu | Val | Glu | Gly | Lys | Pro | Glu | |
| | | 35 | | | | | 40 | | | | | 45 | | | | |
| gct | tcc | aag | agc | ctg | gag | gaa | ata | ata | aag | acc | tcg | tcg | ggg | tcg | gtg | 192 |
| Ala | Ser | Lys | Ser | Leu | Glu | Glu | Ile | Ile | Lys | Thr | Ser | Ser | Gly | Ser | Val | |
| 50 | | | | | 55 | | | | | 60 | | | | | | |
| ctg | aac | aac | gcg | ggc | cag | gcg | tgg | aac | cac | acg | ttc | tac | tgg | aag | tcg | 240 |
| Leu | Asn | Asn | Ala | Gly | Gln | Ala | Trp | Asn | His | Thr | Phe | Tyr | Trp | Lys | Ser | |
| 65 | | | | | 70 | | | | | 75 | | | | | 80 | |
| atg | cgg | ccg | gcc | tcg | gcg | ggg | ggc | ccg | ggg | gcc | ccc | ggc | ggg | ggc | | 288 |
| Met | Arg | Pro | Ala | Ser | Ala | Gly | Gly | Pro | Gly | Ala | Pro | Gly | Gly | Gly | | |
| | | | | 85 | | | | | 90 | | | | | 95 | | |
| ccc | ccg | ggg | gcc | ccg | ggg | gcc | ccc | ctg | cgg | gag | gag | ctg | gag | agc | gcg | 336 |
| Pro | Pro | Gly | Ala | Pro | Gly | Ala | Pro | Leu | Arg | Glu | Glu | Leu | Glu | Ser | Ala | |
| | | | 100 | | | | | 105 | | | | | 110 | | | |
| ttc | ggg | ggc | gtg | gag | aag | ttc | cgg | gag | gcc | ttt | gct | gct | gct | gct | gct | 384 |
| Phe | Gly | Gly | Val | Glu | Lys | Phe | Arg | Glu | Ala | Phe | Ala | Ala | Ala | Ala | Ala | |
| | | 115 | | | | | 120 | | | | | 125 | | | | |
| gcg | cac | ttc | ggc | tcg | ggc | tgg | gcc | tgg | ctc | tgc | ttc | tgc | aag | aag | tcc | 432 |
| Ala | His | Phe | Gly | Ser | Gly | Trp | Ala | Trp | Leu | Cys | Phe | Cys | Lys | Lys | Ser | |
| | | 130 | | | | | 135 | | | | | 140 | | | | |
| cgc | agc | ctc | ttt | ttg | ctg | cag | acc | cac | gac | ggg | gcc | acg | cct | ttc | aga | 480 |
| Arg | Ser | Leu | Phe | Leu | Leu | Gln | Thr | His | Asp | Gly | Ala | Thr | Pro | Phe | Arg | |
| 145 | | | | | 150 | | | | | 155 | | | | | 160 | |
| gac | aac | ccc | aac | tgc | gcg | ccg | ctg | ctc | acc | tgc | gac | ctg | tgg | gag | cac | 528 |
| Asp | Asn | Pro | Asn | Cys | Ala | Pro | Leu | Leu | Thr | Cys | Asp | Leu | Trp | Glu | His | |
| | | | | 165 | | | | | 170 | | | | | 175 | | |

```
gcc tac tac atc gac cgc aga aac gac cgc aag agc tac ctc gac gcg    576
Ala Tyr Tyr Ile Asp Arg Arg Asn Asp Arg Lys Ser Tyr Leu Asp Ala
            180                 185                 190 tgg tgg tct gtg gtg aat tgg gac ttc gcg aac gag aac ttg aag aag    624
Trp Trp Ser Val Val Asn Trp Asp Phe Ala Asn Glu Asn Leu Lys Lys
        195                 200                 205 gca atg cag gga agc gac tag gcgcgtggtg gtctgtggtg aattgggact       675
Ala Met Gln Gly Ser Asp
    210 tcgcgaacga gaacttgaag aaggcaatgc agggaagcga ctag                   719

<210> SEQ ID NO 40
<211> LENGTH: 265
<212> TYPE: DNA
<213> ORGANISM: Eimeria tenella
<220> FEATURE:
<221> NAME/KEY: Intron
<222> LOCATION: (87)..(229)
<223> OTHER INFORMATION: Genomic DNA sequence

<400> SEQUENCE: 40
ttcccggatt ttcaggcgga ggcgctgggc gccgagcact tccgcttgca cgagtacttg     60
ggggacagct ggggagtgat gttcaggtaa gattggcgta aaaaagcccc atttaatcgc    120 attttttaatt ctgtagactc tgtgtcgact gctgagcacg aggggggggc ctgctgcacg   180
ggagagcctt gtctcgcgct caactctggg tttctggcgt tgcttgcagc cacccgaacg    240
acttcacccc cgtctgcacc accga                                         265

<210> SEQ ID NO 41
<211> LENGTH: 672
<212> TYPE: DNA
<213> ORGANISM: Artificial
<220> FEATURE:
<223> OTHER INFORMATION: cDNA
<220> FEATURE:
<221> NAME/KEY: CDS
<222> LOCATION: (1)..(672)

<400> SEQUENCE: 41 atg ccg ttg aac ttg gga gat tcc ttt cca gac ttc cag gcg gag gcg     48
Met Pro Leu Asn Leu Gly Asp Ser Phe Pro Asp Phe Gln Ala Glu Ala
1               5                   10                  15 ctg ggc gcc gag cac ttc cgc ttg cac gag tac ttg ggg gac agc tgg     96
Leu Gly Ala Glu His Phe Arg Leu His Glu Tyr Leu Gly Asp Ser Trp
            20                  25                  30 gga gtg atg ttc agc cac ccg aac gac ttc act ccc gtt tgc aca acg    144
Gly Val Met Phe Ser His Pro Asn Asp Phe Thr Pro Val Cys Thr Thr
        35                  40                  45 gag ctc gcc gaa gcc gtg aag ctc cag gac tcc ttc acg aag aag aac    192
Glu Leu Ala Glu Ala Val Lys Leu Gln Asp Ser Phe Thr Lys Lys Asn
    50                  55                  60 tgc aaa ctc gtt ggc ttc tcc tgc aac gac ctg cag agc cac aga gaa    240
Cys Lys Leu Val Gly Phe Ser Cys Asn Asp Leu Gln Ser His Arg Glu
65                  70                  75                  80 tgg gcg aag gat ata atg gcc tat gca ggc cga tct ggg aac ttg ccg    288
Trp Ala Lys Asp Ile Met Ala Tyr Ala Gly Arg Ser Gly Asn Leu Pro
                85                  90                  95 ttt ccc ctc gtt tgc gac ccc aat agg gaa ctg gcc gcg agt ttg gga    336
Phe Pro Leu Val Cys Asp Pro Asn Arg Glu Leu Ala Ala Ser Leu Gly
            100                 105                 110
```

```
att atg gat cct gca gaa aag gac aaa aag ggg ctg cct ttg act tgc      384
Ile Met Asp Pro Ala Glu Lys Asp Lys Lys Gly Leu Pro Leu Thr Cys
        115                 120                 125 cgc tgc gtc ttt ttc ata agt cca gag aag aag ctc gcg gcc tct att      432
Arg Cys Val Phe Phe Ile Ser Pro Glu Lys Lys Leu Ala Ala Ser Ile
    130                 135                 140 ttg tac ccg gct acc acc ggg aga aac ttc gcg gaa atc ctt agg gtc      480
Leu Tyr Pro Ala Thr Thr Gly Arg Asn Phe Ala Glu Ile Leu Arg Val
145                 150                 155                 160 ctg gac tct ctg cag ctc act gcc aag ttt cca gtg gcc act cca gtg      528
Leu Asp Ser Leu Gln Leu Thr Ala Lys Phe Pro Val Ala Thr Pro Val
                165                 170                 175 gac tgg acc gct ggg gcc aaa tgc tgc gta gtg ccg aac ttg gca gca      576
Asp Trp Thr Ala Gly Ala Lys Cys Cys Val Val Pro Asn Leu Ala Ala
            180                 185                 190 gaa gag gcc caa agg ctt ttg ccc aaa ggc cac gag gcg ctg cag ctg      624
Glu Glu Ala Gln Arg Leu Leu Pro Lys Gly His Glu Ala Leu Gln Leu
        195                 200                 205 cct tcg ggg aag cct tac ctg cgg ctc acc cca gac ccc agg ggc tga      672
Pro Ser Gly Lys Pro Tyr Leu Arg Leu Thr Pro Asp Pro Arg Gly
    210                 215                 220

<210> SEQ ID NO 42
<211> LENGTH: 26
<212> TYPE: DNA
<213> ORGANISM: Artificial Sequence
<220> FEATURE:
<223> OTHER INFORMATION: backward primer for cDNA synthesis
      n=inosine
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 42
tcngtngtrc anacnggngt raartc                                          26

<210> SEQ ID NO 43
<211> LENGTH: 23
<212> TYPE: DNA
<213> ORGANISM: Artificial Sequence
<220> FEATURE:
<223> OTHER INFORMATION: forward primer for cDNA synthesis
      n=inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (18)..(18)
<223> OTHER INFORMATION: n is inosine
```

```
-continued
<400> SEQUENCE: 43
ttyccngayt tycargcnga rgc                                              23
```

COCCIDIOSIS VACCINES

RELATED APPLICATIONS

This application is a divisional of application Ser. No. 10/723,123 filed on Nov. 26, 2003, now U.S. Pat. No. 7,150,873, which is a divisional of application Ser. No. 09/749,233, filed on Dec. 27, 2000, now U.S. Pat. No. 6,680,061, which is a divisional of application Ser. No. 09/411,578, filed on Oct. 4, 1999, now U.S. Pat. No. 6,203,801.

REFERENCE TO SEQUENCE LISTING

The material saved as a "text document" under the file name "AmendedSeq Listing.ST25" created on Mar. 12, 2007 is hereby incorporated by reference.

FIELD OF THE INVENTION

The present invention relates to *Eimeria* polypeptides, DNA-fragments encoding those peptides, recombinant DNA molecules comprising such fragments, live recombinant carriers comprising such fragments or molecules, host cells comprising such fragments, molecules or carriers, antibodies against the polypeptide and coccidiosis vaccines. The invention also relates to methods for the preparation of such antibodies and vaccines, and to methods for the detection of *Eimeria* parasites and antibodies against *Eimeria* parasites.

BACKGROUND OF THE INVENTION

Parasitic protozoa belonging to the genus *Eimeria* are the causative agents of intestinal coccidiosis, an enteritis which affects birds. This causes significant economic loss, especially to the poultry industry. (For the purposes of the present application, the term "poultry" is taken to mean birds that serve as sources of eggs or meat. It includes, inter alia, chickens, turkeys, ducks, geese, guinea fowl, pheasants, pigeons and pea fowl). Nowadays, coccidiosis is mainly controlled by the use of antibiotic drugs in the feed. The rapid emergence of drug resistant strains (Chapman H. D. Parasitology Today 9, 159-162 (1993)) and the prohibitive costs of development and registration of a novel drug have led to increased interest in the development of an alternative method of control. The development of effective vaccines has therefore been desirable for many years. However only partial success has been obtained.

Currently available vaccination strategies consist of controlled infections with either virulent or live attenuated parasites (Shirley M. W. In: Proceedings of the VIth. International Coccidiosis Conference (Eds.: J. R. Barta and M. A. Fernando) Moffitt Print Craft Ltd., Guelph. pp. 61-72 (1993)). For reasons of safety and cost, the most desirable method of immunoprophylaxis against coccidiosis appears to be the use of a subunit vaccine. Although many attempts have been made to immunise chickens against coccidiosis with fractions of parasite material (Murray P. K., Bhogal B. S., Crane M. S. J. & MacDonald T. T. In: Research in Avian Coccidiosis. Proceedings of the Georgia Coccidiosis Conference (Eds.: L. R. McDougald, Joyner L. P. and P. L. Long) Athens, University of Georgia. pp. 564-573 (1986), McKenzie M. E. & Long P. L. Poultry Science 65, 892-897 (1986)) or recombinant *Eimeria* polypeptides (Danforth H. D., Augustine P. C., Ruff M. D., McCandliss R., Strausberg R. L. & Likel M. Poultry Science 68, 1643-1652 (1989), Jenkins M. C., Augustine P. C., Danforth H. D. & Barta J. R. Infection and Immunity 59, 4042-4048 (1991)) only limited protection against challenge infection could be achieved. The parasite stages responsible for the induction of protective immunity are generally thought to be early asexual developmental stages (Jenkins et al., 1991). Initially, selection of candidate antigens was performed using antibodies from immune chickens but, in view of the fundamental role of cell mediated responses in protective immunity (reviewed in Lillehoj H. S. & Trout J. M. Avian Pathology 22, 3-31 (1993), Rose M. E. In: Poultry Immunology (Ed.: T. F. Davison, T. R. Morris and L. N. Payne), Carfax Publishing Company, Oxfordshire, U.K. pp. 265-299 (1996), attention has now focused, next to B-cell inducing antigens, on screening antigens for their ability to stimulate specific T-cell responses (Dunn P. P. J., Billington K., Bumstead J. M. & Tomley F. M. Molecular and Biochemical Parasitology 70, 211-215 (1995)).

It is an objective of the present invention to provide polypeptides that are capable of inducing protection against the pathogenic effects of *Eimeria* infection in poultry.

SUMMARY OF THE INVENTION

It was now surprisingly found that 6 different polypeptides could be specifically identified and isolated, essentially free from other *Eimeria* polypeptides, from a hydrophilic fraction of *Eimeria* polypeptides, each of these different polypeptides being capable of inducing an immune response against *Eimeria* parasites. The inventors have found that these polypeptides can be used, either alone or in combination with each other, to provide a vaccine which gives a significant degree of protection to birds (preferably poultry). For example, protection against the formation of cecal lesions can be achieved in birds immunised with such a vaccine, when subjected to subsequent challenge with *Eimeria* parasites.

DETAILED DESCRIPTION OF THE INVENTION

A first embodiment of the invention relates to a hydrophilic polypeptide of *Eimeria* that in its full-length form has a molecular weight of 25 kD and comprises an amino acid sequence that shares at least 70% homology with the amino acid sequence MPFELPPLPYPMDALEPYISKETLEYHY-GKHHMYVNNLNRLVEGKPEASKSLEEIIKTSSGSVL-NNAGQAWNHTFYWKSMRPASAGGPPGAPGGGPPG-APGAPLREELESAFGGVEKFREAFAAAAAAHFGSG-WAWLCFCKKSRSLFLLQTHDGATPFRDNPNCAPLLT-CDLWEHAYYIDRRNDRKSYLDAWWSVVNWDFANE-NLKKAMQGSD (further referred to as SEQ ID NO: 1:) and immunogenic fragments of that polypeptide capable of inducing an immune response against said polypeptide. The polypeptide is functionally related to a Superoxide Dismutase (SOD) found in non-*Eimeria* parasites and is therefore characterised as SOD-like.

Also, this embodiment relates to a hydrophilic polypeptide of *Eimeria* that is a peroxidoxin-like polypeptide, in its full-length form has a molecular weight of 22 kD and comprises an amino acid sequence that shares at least 70% homology with the amino acid sequence LGPLALPLLADVR (further referred to as SEQ ID NO: 2:), and immunogenic fragments of the polypeptide capable of inducing an immune response against that polypeptide.

A hydrophilic polypeptide of *Eimeria* that is a peroxidoxin-like polypeptide, in its full-length form has a molecular weight of 25 kD and comprises an amino acid sequence that shares at least 70% homology with the amino acid sequence MPLNLGDSFPDFQAEALGAEHFRLHEYLGDSWGV-MFSHPNDFTPVCTTELAEAVKLQDSFTKKNCKLVGF-SCNDLQSHREWAKDIMAYAGRSGNLPFPLVCDPNR- ELAASLGIMDPAEKDKKGLPLTCRCVFFISPEKKLAA-SILYPATTGRNFAEILRVLDSLQLTAKFPVATPVDWTA-GAKCCVVPNLAAEEAQRLLPKGHEALQLPSGKPYL-RLTPDPRG (further referred to as SEQ ID NO: 3:), as well as immunogenic fragments of the polypeptide capable of inducing an immune response against that polypeptide are also part of this embodiment.

Also part of this embodiment is a hydrophilic polypeptide of *Eimeria* that in its full-length form has a molecular weight of 22 kD and comprises an amino acid sequence that shares at least 70% homology with the amino acid sequence MSPSPAGVAEYLASL (further referred to as SEQ ID NO: 4:), or an immunogenic fragment of that polypeptide capable of inducing an immune response against said polypeptide.

This embodiment also includes a triosephosphate isomerase-like hydrophilic polypeptide of *Eimeria* that in its full-length form has a molecular weight of 28 kD and comprises an amino acid sequence that shares at least 70% homology with the amino acid sequence NHAEFDPSQTEVVVFP (further referred to as SEQ ID NO: 5:), or an immunogenic fragment of that polypeptide capable of inducing an immune response against said polypeptide.

Finally, this embodiment relates to a hydrophilic polypeptide of *Eimeria* that in its full-length form has a molecular weight of 28 kD and comprises an amino acid sequence that shares at least 70% homology with the amino acid sequence VDSFTPSVGCVFAGMPADFR (further referred to as SEQ ID NO: 6:), or an immunogenic fragment of that polypeptide capable of inducing an immune response against said polypeptide.

Although various groups have disclosed *Eimeria* derived proteins which might, by chance, have molecular masses within the 26-30 kDa±5 kDa range disclosed above, these proteins are quite different from the polypeptides of the present invention.

For example, in EP-A-0231537 (Newman et al) a 25 kDa surface protein is disclosed. However under reducing conditions this splits to form two bands on SDS-PAGE of about 17 and about 8 kDa, whereas the polypeptides of the present invention had relative molecular masses of at least 21 kDa when separated under reducing conditions.

Bouvier et al (*J. Biol. Chem.* (1985) 260(29); pp 15504-15509) teach that using Triton X114 extraction amphiphilic proteins (membrane-associated) are only detected in the detergent phase and not in the hydrophilic phase.

In U.S. Pat. No. 4,710,377 (Schenkel et al) antigens are disclosed with molecular masses of about 28 and 26 kDa. However these are amphiphilic outer-membrane components and would not therefore be present in the hydrophilic phase of a Triton X-114 extract which could be used to prepare polypeptides of the present invention.

*Eimeria* proteins that are amphiphilic are also disclosed in WO92/04461 (Jacobson et al), EP-A-0324648 (Liberator et al), AU-A-28542/49 (Turner et al), EP-A-0344808 (Alternburger et al) and EP-A-0167443 (Murray et al).

It will be understood that, for the particular hydrophilic polypeptides embraced herein, natural variations can exist between individual *Eimeria* parasites or strains. These variations may exist in (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (*Science,* 227, 1435-1441, 1985) and determining the functional similarity between homologous proteins. Such amino acid substitutions of the exemplary embodiments of this invention are within the scope of the invention as long as the resulting polypeptides retain their immunoreactivity. Thus, natural variations not essentially influencing the immunogenicity of the polypeptide compared to the wild-type polypeptide, are considered immunologically equivalent variants of the polypeptides according to the invention.

Therefore, a polypeptide having a variant amino acid sequence, that has at least 70% homology to respectively the amino acid sequence MPFELPPLPYPMDALEPYISKET-LEYHYGKHHAAYVNNLNRLVEGKPEASKSLEEIIKT-SSGSVLNNAGQAWNHTFYWKSMRPASAGGPPGAPG-GGPPGAPGAPLREELESAFGGVEKFREAFAAAAAA-HFGSGWAWLCFCKKSRSLFLLQTHDGATPFRDNPNC-APLLTCDLWEHAYYIDRRNDRKSYLDAWWSVVNW-DFANENLKKAMQGSD, LGPLALPLLADVR, MPLNLG-DSFPDFQAEALGAEHFRLHEYLGDSWGVMFSHPND-FTPVCTTELAEAVKLQDSFTKKNCKLVGFSCNDLQS-HREWAKDIMAYAGRSGNLPFPLVCDPNRELMSLGIM-DPAEKDKKGLPLTCRCVFFISPEKKLAASILYPATTGR-NFAEILRVLDSLQLTAKFPVATPVDWTAGAKCCVVP-NLAAEEAQRLLPKGHEALQLPSGKPYLRLTPDPRG, MSPSPAGVAEYLASL, NHAEFDPSQTEVVVFP and VDSFTPSVGCVFAGMPADFR as depicted in SEQ ID NO: 1-6 is also considered to fall within the scope of the invention.

The level of homology is defined by the following formula: H=m/n×100%, wherein H is the percentage homology, m is the number of identical amino acids in the sequence and n is the total number of amino acids. The amino acid sequence ABCDEEGHIJK, when compared to ABCDEFGHIJK, would then be 10/11×100%=90.9% homologous. The amino acid sequence ABCDEGHIJK would also be 10/11×100%=90.9% homologous: there would just be a gap at the spot where one sequence has the F and the other sequence has not.

When a polypeptide is used for e.g. vaccination purposes or for raising antibodies, it is however not necessary to use the whole polypeptide. It is also possible to use a fragment of that polypeptide that is capable of inducing an immune response against that polypeptide, a so-called immunogenic fragment.

An "immunogenic fragment" is understood to be a fragment of the full-length protein, that still has retained its capability to induce an immune response in the host. At this moment, a variety of techniques is available to easily identify antigenic fragments (determinants). The method described by Geysen et al (Patent Application WO 84/03564, Patent Application WO 86/06487, U.S. Pat. No. 4,833,092, Proc. Natl. Acad. Sci. 81: 3998-4002 (1984), J. Imm. Meth. 102, 259-274 (1987), the so-called PEPSCAN method is an easy to perform, quick and well-established method for the detection of epitopes; the immunologically important regions of the protein, used world-wide and as such well-known to man skilled in the art. This (empirical) method is especially suitable for the detection of B-cell epitopes. Also, given the sequence of the gene encoding any protein, computer algorithms are able to designate specific polypeptide fragments as the immunologically important epitopes on the basis of their sequential and/or structural homology with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47: 45-148 (1987) and U.S. Pat. No. 4,554,101).

T-cell epitopes can likewise be predicted from the sequence by computer with the aid of Berzofsky's amphiphilicity criterion (Science 235, 1059-1062 (1987) and U.S. patent application NTIS U.S. Ser. No. 07/005,885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzofsky for HIV-epitopes; The FASEB Journal 5:2412-2418 (1991)

Therefore, this embodiment of the invention not only relates to polypeptides according to the invention, but also to fragments of those polypeptides that are still capable of inducing an immune response against the polypeptides (so-called immunogenic fragments).

In a preferred form of this embodiment, a hydrophilic polypeptide is provided, that comprises an amino acid sequence that is at least 80% homologous to the sequence given in one of the SEQ ID NO: 1-6.

In a more preferred form of this embodiment, the amino acid sequence is at least 90% homologous to the sequence given in one of the SEQ ID NO: 1-6.

In an even more preferred form of this embodiment, the amino acid sequence is the sequence given in one of the SEQ ID NO: 1-6.

Preferably the polypeptide according to the invention is isolated from *Eimeria tenella*.

Another embodiment of the invention relates to DNA fragments encoding a polypeptide of the present invention or immunogenic fragments thereof. Since for the first time the partial amino acid sequence of the polypeptides according to the invention is now provided, man skilled in the art can (using the genetic code table found in biochemistry textbooks as e.g. in Lubert Stryer's Biochemistry, Ed. Freeman and Company, New York) easily prepare a mixed DNA probe and select the gene encoding the polypeptide according to the invention from *Eimeria*.

There may be minor variations in the overall nucleotide sequence of the DNA encoding the polypeptides according to the invention in the respective *Eimeria* strains. These variations may have no effect on the amino acid sequence of the polypeptide, in case that the modification is such that the variant triplet codes for the same amino acid. This cause of variation is based upon the phenomenon of degeneracy of the genetic code. It happens e.g. that due to natural mutation the G in the triplet CTG, coding for the amino acid Leucine, is replaced by a C, also coding for Leucine, or that the A in GAA coding for glutamic acid is replaced by a G, which triplet still encodes glutamic acid. Such a mutation is a silent mutation, i.e. it does not show at the amino acid level. Such silent modifications are very frequently found in nature, when comparing e.g. two different field isolates of *Eimeria*. This phenomenon is found for all amino acids, except Met and Trp. Thus, it is obvious, that the polypeptides of the present invention can be encoded by a very large variety of other sequences, all encoding the identical polypeptide. It therefore goes without saying that any nucleic acid sequence encoding a polypeptide comprising an amino acid sequence that is at least 70% homologous to the amino acid sequence as depicted in SEQ ID NO: 1-6 of the present invention or an immunogenic fragment thereof is also considered to fall within the scope of the invention.

Merely for the purpose of giving an example, all possible probes for detecting the gene encoding the 25 kD SOD-like hydrophilic *Eimeria* polypeptide comprising i.a. the amino acid sequence YLDAWWSVVNWDFANENLK (part of SEQ ID NO: 1:) are given in SEQ ID NO: 7-38. In these SEQ IDs, all possible nucleic acid sequences are listed that code for the amino acid sequence VNWDFA of SEQ ID NO: 1:. Of the 32 probes, one has by definition a perfect fit with each DNA fragment comprising a nucleic acid sequence encoding a polypeptide comprising an amino acid sequence of SEQ ID NO: 1.

As described i.a. in Maniatis/Sambrook (Sambrook, J. et al., Molecular cloning: a laboratory manual. ISBN 0-87969-309-6) hybridisation of probes to DNA is done at 12° C. below Tm, where Tm=69.3+0.41×(G+C) %−650/L (L=length of the probe). That means that under stringent conditions (a hybridisation temperature of between 38 and 48 degrees Celsius), the gene encoding a polypeptide comprising an amino acid sequence of SEQ ID NO: 1 can always be picked up selectively and free from false hybridisation signals, using the probes of SEQ ID NO: 7-38. Such mixed probes very easily made using standard procedures in e.g. one of the many commercially available automatic DNA synthesizers.

For the reasons given above, especially a mixed DNA probe encoding the whole amino acid sequence of one of the amino acid sequences given in SEQ ID NO: 1-6 can be used to detect the genes encoding the polypeptides according to the invention in *Eimeria*.

Identification and cloning of the genes encoding the polypeptides according to the invention in *Eimeria*, not only for *tenella* but also for the other species, can easily be done as follows: first strand cDNA can be hybridised with both a mixed probe for one of the polypeptides according to the invention and an oligo-dT probe. The DNA fragment between both probes can then be multiplied in a standard PCR reaction. (PCR-techniques are e.g. described in Maniatis/Sambrook (Sambrook, J. Molecular cloning: a laboratory manual. ISBN 0-87969-309-6)). The PCR fragment can then be cloned into a plasmid and e.g. be used for sequencing or for detection of the full length gene in the genome of any *Eimeria* species.

This method allows an easy and straightforward selection and sequencing of the genes encoding the polypeptides according to the invention, not only from *Eimeria tenella* but also from other *Eimeria* species such as *necatrix, brunetti, mitis* or *acervulina*.

Thus, in another embodiment, the invention relates to a DNA fragment comprising a nucleotide sequence encoding a polypeptide according to the invention or an immunogenic fragment thereof.

The mixed probe method described above for the detection of the DNAs encoding the various polypeptides according to the invention has e.g. been used to obtain the DNA encoding the 25 kD SOD-like polypeptide according to the invention in *Eimeria tenella*. Using the method described in the Examples, a DNA fragment encoding practically the whole 25 kD SOD-like polypeptide of *Eimeria tenella* could be isolated, cloned and sequenced. The sequence of that DNA-fragment was found to be ATGCCGTTCGAACTCCCC-CGCTGCCGTACCCCATGGACGCCCTCGAGCCGTAC-ATCAGCAAAGAGACTCTCGAGTACCACTATGGGAA-GCACCACGCGGCTTACGTGAACAACTTGAACAGAC-TCGTCGAGGGGAAGCCGGAGGCTTCCAAGAGCCT-GGAGGAAATAATAAAGACCTCCTCGGGGTCGGTG-CTGAACAACGCGGGCCAGGCGTGGAACCACACGT-TCTACTGGAAGTCGATGCGGCCGGCCTCGGCGGG- GGGCCCCCCGGGGGCCCCCGGCGGGGGCCCCCCG-
GGGGCCCCGGGGGCCCCCCTGCGGGAGGAGCTG-
GAGAGCGCGTTCGGGGGCGTGGAGAAGTTCCGGG-
AGGCCTTTGCTGCTGCTGCTGCTGCGCACTTCGGC-
TCGGGCTGGGCCTGGCTCTGCTTCTGCAAGMGTC-
CCGCAGCCTCTTTTTGCTGCAGACCCACGACGGGG-
CCACGCCTTTCAGAGACAACCCCAACTGCGCGCC-
GCTGCTCACCTGCGACCTGTGGGAGCACGCCTACT-
ACATCGACCGCAGAAACGACCGCAAGAGCTACCT-
CGACGCGTGGTGGTCTGTGGTGAATTGGGACTTCG-
CGAACGAGAACTTGAAGMGGCAATGCAGGGAAGC-
GACTAGGCGCGTGGTGGTCTGTGGTGAATTGGGA-
CTTCGCGAACGAGAACTTGAAGAAGGCAATGCAG-
GGAAGCGACTAG and will be further referred to as SEQ ID NO: 39:

Therefore a preferred form of this embodiment relates to a DNA fragment comprising a nucleotide sequence as depicted in SEQ ID NO: 39:

The mixed probe method was also used to obtain the DNA encoding the 25 kD peroxidoxin-like polypeptide according to the invention in *Eimeria tenella*. Using the method described in the Examples, a DNA fragment encoding a large part of the whole 25 kD peroxidoxin-like polypeptide of *Eimeria tenella* could be isolated, cloned and sequenced. In addition, the genomic sequence, i.e. the sequence of the part of the gene as found in the *Eimeria tenella* genome was found to be TTCCCGGATTTTCAGGCGGAGGCGCTGGGCG-
CCGAGCACTTCCGCTTGCACGAGTACTTGGGGGAC-
AGCTGGGGAGTGATGTTCAGgtaagattggcgtaaaaaagcc-
ccatttaatcgcatttttaattctgtagactctgtgtcgactgctgagcacgagggggg-
gggcctgctgcacgggagagccttgtctcgcgctcaactctgggttttctggcgttg-
cttgcagCCACCCGAACGACTTCACCCCCGTCTGCAC-
CACCGA. This sequence is further referred to as SEQ ID NO: 40:

Upper case letters indicate the sequence also found in the mRNA, small letters indicate the intron in the gene.

Therefore another preferred form of this embodiment relates to a DNA fragment comprising a nucleotide sequence as depicted in SEQ ID NO: 40:

The cDNA encoding the mRNA for this polypeptide was also detected using the mixed probe approach. This cDNA was sequenced and found to have the following sequence:
ATGCCGTTGAACTTGGGAGATTCCTTTCCAGACTT-
CCAGGCGGAGGCGCTGGGCGCCGAGCACTTCCGC-
TTGCACGAGTACTTGGGGGACAGCTGGGGAGTGA-
TGTTCAGCCACCCGAACGACTTCACTCCCGTTTGC-
ACAACGGAGCTCGCCGAAGCCGTGAAGCTCCAGG-
ACTCCTTCACGAAGMGAACTGCAAACTCGTTGGCT-
TCTCCTGCAACGACCTGCAGAGCCACAGAGAATGG-
GCGAAGGATATAATGGCCTATGCAGGCCGATCTGG-
GAACTTGCCGTTTCCCCTCGTTTGCGACCCCAATA-
GGGAACTGGCCGCGAGTTTGGGAATTATGGATCCT-
GCAGAAAAGGACAAAAAGGGGCTGCCTTTGACTT-
GCCGCTGCGTCTTTTTCATAAGTCCAGAGAAGMGC-
TCGCGGCCTCTATTTTGTACCCGGCTACCACCGGG-
AGAAACTTCGCGGAAATCCTTAGGGTCCTGGACTC-
TCTGCAGCTCACTGCCAAGTTTCCAGTGGCCACTC-
CAGTGGACTGGACCGCTGGGGCCAAATGCTGCGTA-
GTGCCGAACTTGGCAGCAGAAGAGGCCCAAAGGC-
TTTTGCCCAAAGGCCACGAGGCGCTGCAGCTGCCT-
TCGGGGAAGCCTTACCTGCGGCTCACCCCAGACCC-
CAGGGGCTGA. This sequence is further referred to as SEQ ID NO: 41:

Thus, still another preferred form of this embodiment relates to a DNA fragment comprising a nucleotide sequence as depicted in SEQ ID NO: 41:

The polypeptides of the present invention can be isolated from *Eimeria* parasites using any standard isolation procedure known in the art for isolating *Eimeria* polypeptides. The polypeptides are e.g. obtainable as described in the Examples. They can be used subsequently for e.g. the preparation of a vaccine or for raising antibodies.

Alternatively a DNA fragment according to the invention can be expressed in an in vitro expression system and the expression product, the polypeptide according to the invention, can be used e.g. for vaccine or antibody preparations.

An essential requirement for the expression of the DNA fragment is an adequate promoter operably linked to the fragment. It is obvious to those skilled in the art that the choice of a promoter extends to any eukaryotic, prokaryotic or viral promoter capable of directing gene transcription in cells used as host cells for protein expression.

Therefore, a preferred form of this embodiment relates to recombinant DNA fragments, i.e. DNA fragments according to the invention, to which regulating sequences enabling expression of that nucleic acid sequence have been added by means of e.g. standard molecular biology techniques. (Maniatis/Sambrook (Sambrook, J. Molecular cloning: a laboratory manual. ISBN 0-87969-309-6))

When the host cells are bacteria, useful expression control sequences which may be used include the Trp promoter and operator (Goeddel, et al., *Nucl. Acids Res.*, 8, 4057, 1980); the lac promoter and operator (Chang, et al., *Nature*, 275, 615, 1978); the outer membrane protein promoter (Nakamura, K. and Inouge, M., *EMBO J.*, 1, 771-775, 1982); the bacteriophage lambda promoters and operators (Remaut, E. et al., *Nucl. Acids Res.*, 11, 4677-4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., *Mol. Cell. Biol.* 3, 2156-65, 1983). When the host cell is of mammalian origin illustrative useful expression control sequences include the SV-40 promoter (Berman, P. W. et al., *Science*, 222, 524-527, 1983) or the metallothionein promoter (Brinster, R. L., *Nature*, 296, 3942, 1982) or a heat shock promoter (Voellmy et al., *Proc. Natl. Acad. Sci. USA*. 82, 4949-53, 1985). Alternatively, expression control sequences present in *Eimeria* may also be applied. For maximising gene expression, see also Roberts and Lauer (*Methods in Enzymology*, 68, 473, 1979).

Bacterial, yeast, fungal, insect and mammalian cell expression systems are very frequently used systems. Such systems are well-known in the art and easily available, e.g. commercially through Clontech Laboratories, Inc. 4030 Fabian Way, Palo Alto, Calif. 94303-4607, USA. Next to these expression systems, parasite-based expression systems are very attractive expression systems. Such systems are e.g. described in the French Patent Application with Publication number 2 714 074, and in U.S. Ser. No. 08/043,109 (Hoffman, S and Rogers, W.: public. Date 1 Dec. 1993).

Therefore, in a more preferred form of this embodiment the invention relates to a recombinant DNA molecule encoding the polypeptide fragment under the control of regulating sequences enabling expression of the protein encoded by said nucleic acid sequence.

Another embodiment of the invention relates to Live Recombinant Carriers (LRCs) comprising a DNA fragment or a recombinant DNA molecule according to the invention encoding a polypeptide according to the invention or an immunogenic fragment thereof. Such Live Recombinant Carriers are e.g. bacteria, parasites and viruses. These LRC micro-organisms are micro-organisms in which additional genetic information has been cloned. Animals infected with such LRCs will produce an immunogenic response not only against the immunogens of the LRC, but also against the immunogenic parts of the polypeptide(s) for which the genetic code is additionally cloned into the LRC, e.g. the polypeptide according to the invention.

As an example of bacterial LRCs, attenuated *Salmonella* strains known in the art can attractively be used. Also, LRC viruses may be used as a way of transporting the DNA fragment into a target cell.

Live recombinant carrier parasites have i.a. been described by Vermeulen, A. N. (Int. Journ. Parasitol. 28: 1121-1130 (1998))

Live recombinant carrier viruses are also called vector viruses. The site of integration of the DNA encoding the polypeptide according to the invention or an immunogenic fragment thereof may be a site in a viral gene that is not essential to the virus, or a site in an intergenic region. Viruses often used as vectors are Vaccinia viruses (Panicali et al; Proc. Natl. Acad. Sci. USA, 79: 4927. (1982), Herpesviruses (E.P.A. 0473210A2), and Retroviruses (Valerio, D. et al; in Baum, S. J., Dicke, K. A., Lotzova, E. and Pluznik, D. H. (Eds.), Experimental Haematology today—1988. Springer Verlag, New York: pp. 92-99 (1989)).

Especially fowlpox virus, a vaccinia virus infectious to poultry, and Herpesvirus of Turkeys (HVT) are very attractive live recombinant carrier viruses for carrying DNA encoding a polypeptide of the invention or an immunogenic fragment thereof.

The invention also relates to a host cell containing a DNA fragment according to the invention, to a host cell containing a recombinant DNA molecule containing a DNA fragment according to the invention under the control of regulating sequences enabling expression of the protein encoded by said nucleic acid sequence and to a host cell containing a Live Recombinant Carrier micro-organism (LCR) containing a DNA fragment according to the invention.

A host cell may be a cell of bacterial origin, e.g. *Escherichia coli, Bacillus subtilus* and *Lactobacillus* species, in combination with bacteria-based vectors as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

The technique of in vivo homologous recombination, well-known in the art, can be used to introduce a recombinant nucleic acid sequence into the genome of a bacterium, parasite or virus of choice, capable of inducing expression of the inserted gene in the host animal.

Another embodiment of the invention relates to vaccines capable of protecting poultry against the pathogenic effects of *Eimeria* infection. Vaccines according to the present invention can be made e.g. by merely admixing of a polypeptide according to the invention or an immunogenic fragment thereof and a pharmaceutically acceptable carrier. A pharmaceutically acceptable carrier is understood to be a compound that does not adversely effect the health of the animal to be vaccinated, at least not to the extend that the adverse effect is worse than the effects seen due to illness when the animal is not vaccinated. A pharmaceutically acceptable carrier can be e.g. sterile water or a sterile physiological salt solution. In a more complex form, the carrier can e.g. be a buffer.

The vaccine according to the present invention may in a preferred presentation also contain an adjuvant. Adjuvants in general comprise substances that boost the immune response of the host in a non-specific manner. A number of different adjuvants are known in the art. Examples of adjuvants are Freunds Complete and Incomplete adjuvant, vitamin E, non-ionic block polymers and polyamines such as dextransulphate, carbopol and pyran. Also very suitable are surface active substances such as Span, Tween, hexadecylamine, lysolecitin, methoxyhexadecylglycerol and saponins such as Quill A®. A preferred adjuvant is Quill A. This may be administered at a level of around 150 µg/dose (for example). Furthermore, peptides such as muramyldipeptides, dimethylglycine, tuftsin, are often used. Next to these adjuvants, Immune-stimulating Complexes (ISCOMS), mineral oil e.g. Bayol® or Markol®, vegetable oils or emulsions thereof and Diluvac® Forte can advantageously be used. The vaccine may also comprise a so-called "vehicle". A vehicle is a compound to which the polypeptide adheres, without being covalently bound to it. Often used vehicle compounds are e.g. aluminium hydroxide, -phosphate, sulphate or -oxide, silica, Kaolin, and Bentonite. A special form of such a vehicle, in which the antigen is partially embedded in the vehicle, is the so-called ISCOM (EP 109.942, EP 180.564, EP 242.380). A preferred adjuvant is Quill A. This may be administered at a level of around 150 µg/dose (for example).

Often, the vaccine is mixed with stabilisers, e.g. to protect degradation-prone polypeptides from being degraded, to enhance the shelf-life of the vaccine, or to improve freeze-drying efficiency. Useful stabilisers are i.a. SPGA (Bovarnik et al; J. Bacteriology 59: 509 (1950)), skimmed milk, gelatin, bovine serum albumin, carbohydrates e.g. sorbitol, mannitol, trehalose, starch, sucrose, dextran or glucose, proteins such as albumin or casein or degradation products thereof, and buffers, such as alkali metal phosphates.

Freeze-drying is an efficient method for conservation. Freeze-dried material can be stored and kept viable for many years. Storage temperatures for freeze-dried material may well be above zero degrees, without being detrimental to the material.

Freeze-drying can be done according to all well-known standard freeze-drying procedures.

Therefore, in a most preferred embodiment, the vaccine is in a freeze-dried form.

In addition, the vaccine may be suspended in a physiologically acceptable diluent. Such a diluent can e.g. be as simple as sterile water, or a physiological salt solution.

It goes without saying, that other ways of adjuvating, adding vehicle compounds or diluents, emulsifying or stabilising a polypeptide are also embodied in the present invention.

The vaccine according to the invention can be administered in a conventional active immunisation scheme: single or repeated administration in a manner compatible with the dosage formulation, and in such amount as will be prophylactically effective, i.e. the amount of immunising antigen or recombinant micro-organism capable of expressing said antigen that will induce immunity in birds (especially poultry) against challenge by virulent *Eimeria* parasites. Immunity is defined as the induction of a significant level of protection in a population of birds after vaccination compared to an unvaccinated group.

A vaccine comprising the polypeptide of the invention may reduce the number of oocysts shedded by the infected animals. Normally, the shedded oocysts will infect other animals in the flock. A decrease in the number of oocysts shedded will then also give a decrease in the number of animals which is subsequently infected and also a decrease in the number of oocysts shedded will give rise to a lesser infectious load.

Furthermore, even without effect on the parasite itself, a vaccine may decrease the incidence of disease. This is especially so when the symptoms of the disease are caused by products released by the parasite. Vaccines directed against such products alleviate the symptoms without attacking the parasite.

In any event it is preferred that a vaccine of the present invention is capable of reducing the number of cecal lesions in a bird when challenged with a subsequent *Eimeria* infection.

For live viral vector vaccines the dose rate per chicken may range from $10^3$ to $10^8$ pfu (but even <1000 pfu might be sufficient e.g. for HVT). A typical subunit vaccine according to the invention comprises 0.1 to 100 μg of the polypeptide (or variant or fragment thereof) according to the invention. Preferably at least 5 μg will be present. Such vaccines can be administered intradermally, subcutaneously, intramuscularly, intraperitoneally, intravenously, orally or intranasally.

The vaccine according to the invention can also be effectively mixed with other antigenic components of the same and/or other *Eimeria* species, and/or with additional immunogens derived from a poultry pathogenic virus or microorganism and/or nucleic acid sequences encoding these immunogens.

Such a combination vaccine can decrease the parasitic load in a flock of birds and can increase the level of protection against coccidiosis, and in addition protect against other poultry pathogens.

Those other immunogens may e.g. be selected from the group of poultry pathogenic viruses or micro-organisms consisting of Marek's Disease virus (MDV), Newcastle Disease virus (NDV), Infectious Bronchitis virus (IBV), Chicken Anaemia Agent (CAA), Reo virus, Avian Retro virus, Fowl Adeno virus, Turkey Rhinotracheitis virus, *Salmonella* spp. or *E. Coli*. Thus a multivalent vaccine may be provided.

Still another embodiment of the invention relates to methods for the preparation of a vaccine.

Such methods comprise the admixing of a polypeptide according to the invention or an immunogenic fragment thereof and a pharmaceutically acceptable carrier.

An alternative and efficient way of vaccination is direct vaccination with DNA encoding the relevant antigen. Direct vaccination with DNA encoding polypeptides has been successful for many different polypeptides. (As reviewed in e.g. Donnelly et al., The Immunologist 2: 20-26 (1993)). In the field of anti-parasite vaccines, protection against e.g. *Plasmodium yoelii* has been obtained with DNA-vaccination with the *Plasmodium yoelii* circumsporozoite gene (Vaccine 12: 1529-1533 (1994)). Protection against *Leishmania major* has been obtained with DNA-vaccination with the *Leishmania major* surface glycoprotein gp63 gene (Vaccine 12: 1534-1536 (1994)).

Antibodies or derivatives thereof (e.g. fragments such as Fab, F(ab')$_2$ or Fv fragments), which are directed against a polypeptide according to the invention have potential uses in passive immunotherapy, diagnostic immunoassays and in the generation of anti-idiotypic antibodies. Preferably these are specific for the *Eimeria* polypeptides of the present invention or variants/fragments thereof. Serum comprising antibodies or derivatives thereof may also be provided.

The *Eimeria* polypeptides (or variants or fragments thereof) as characterised above can be used to produce antibodies, which may be polyclonal, monospecific or monoclonal (or derivatives thereof). If polyclonal antibodies are desired, techniques for producing and processing polyclonal sera are known in the art (e.g. Mayer and Walter, eds. *Immunochemical Methods in Cell and Molecular Biology*, Academic Press, London, 1987).

Monoclonal antibodies, reactive against the *Eimeria* polypeptides (or variants or fragments thereof according to the present invention, can be prepared by immunising inbred mice by techniques known in the art (Kohler and Milstein, Nature, 256, 495-497, 1975).

Anti-idiotypic antibodies are immunoglobulins which carry an "internal image" of the antigen of the pathogen against which protection is desired and can be used as an immunogen in a vaccine (Dreesman et al., *J. Infect. Disease*, 151, 761, 1985). Techniques for raising anti-idiotypic antibodies are known in the art (MacNamara et al., Science 226, 1325, 1984).

Antibodies against any of the polypeptides of the present invention and made e.g. in one of the manners described above, can be used i.a. for vaccination purposes, especially in immunocompromised animals.

Therefore, still another embodiment of the present invention relates to antibodies against any of the polypeptides according to the invention.

Also the invention relates to methods for the preparation of such antibodies. Those methods comprise the administration of a polypeptide according to the invention to a suitable animal, i.e. an animal capable of making antibodies against polypeptides.

It may be desirable to detect *Eimeria* as the cause of disease in poultry: especially early detection of *Eimeria* infection in a flock offers the opportunity to take adequate measures for the prevention of spreading of the infection. Detection of *Eimeria* infection can be done by detecting the *Eimeria* parasite in the host or by detecting host antibodies against *Eimeria*.

Detection of *Eimeria* parasites can be done e.g. as follows: DNA prepared from the contents of the digestive tract of a sick animal can be probed with DNA fragments according to the invention and submitted to standard Polymerase Chain Reaction (PCR). If *Eimeria* DNA is present, even in extremely low amounts, this will result in a PCR-product, visible on standard agarose gels after several rounds of PCR. PCR-techniques are e.g. described in Maniatis/Sambrook (Sambrook, J. Molecular cloning: a laboratory manual. ISBN 0-87969-309-6)

Therefore, the invention in still another embodiment relates to methods for the detection of *Eimeria*, which methods comprise incubating a DNA preparation isolated from poultry with a DNA fragment according to the invention.

Alternatively, antibodies against *Eimeria* can be detected. Detection of antibodies can e.g. be done using an ELISA assay, in which a polypeptide according to the invention is coated to the wall of an ELISA plate. The first step of such an ELISA may e.g. comprise adding serum of the animal to be tested to the ELISA plate. Antibodies against *Eimeria*, if present at all will bind to the polypeptide coated to the wall. The absence or presence of these antibodies can in a next step i.a. be detected by incubation with a labelled anti-poultry antibody. If antibodies against *Eimeria* were present in the serum to be tested, the labelled anti-poultry antibody will bind to them and the label will reveal their presence. These standard techniques are extensively described in "Antibodies: a laboratory manual" by Harlow, E. and Lane D. ISBN 0-87969-314-2

Therefore, the invention in still another embodiment relates to methods for the detection of *Eimeria*, which methods comprise the detection of host anti-*Eimeria* antibodies against any of the polypeptides according to the present invention.

EXAMPLES

Example 1

Isolation of Proteins and Protein Sequencing

Chickens

Outbred unsexed White Leghorn chickens, raised under specific-pathogen-free conditions, were kept in isolators with free access to food and water. Faeces were monitored weekly to assure that the animals were free of unwanted coccidial infections. For infection chickens were used at 5-7 weeks of age. For vaccination 3 week old chickens were used.

Parasites and Purification of Sporozoites

The Weybridge strain of *E. tenella* was used (Shirley M. W. In: *Research in Avian Coccidiosis. Proceedings of the Georgia Coccidiosis Conference* (Eds.: L. R. McDougald, Joyner L. P. and P. L. Long) Athens, University of Georgia. pp. 13-35 (1986)). The parasites were passaged at regular intervals through coccidia-free chickens. Handling of oocysts, release of sporocysts and sporozoites from sporulated oocysts was performed as described earlier (Long P. L., Millard B. J., Joyner L. P. & Norton C. C. *Folia Veterinaria Latina* 6, 201-217 (1976)) using 0.4% taurocholate (Sigma, St. Louis, Mo., USA) instead of bile salts (Toyama T. & Kitano N. *Japanese Journal of Veterinary Science* 45, 139-141 (1983)). The sporozoites were further purified by nylon wool passage (Larsen R. A., Kyle J. E., Whitmire W. M. & Speer C. A. *Journal of Parasitology* 70, 597-601 (1984)) and stored as pellets at −70° C.

Sporozoite Protein Fractionation

Triton-X114 Extraction

A Triton X-114 extraction was performed to isolate the hydrophilic phase of total sporozoite proteins (HPS) (Bordier C. *Journal of Biological Chemistry* 256, 1604-1607 (1981)). Hereto, $5 \times 10^9$ purified *E. tenella* sporozoites were suspended ($2 \times 10^8$/ml) in 10 mM Tris-HCl, 150 mM NaCl pH 7.4 (TBS) supplemented with DNAse (20 µg/ml) and protease inhibitors; 1 mM phenylmethyl sulfonyl fluoride (PMSF, Serva, Heidelberg, Germany), 5 µg/ml Aprotinine, 1 µg/ml Leupeptin and 1 µg/ml Pepstatin A and sonified three times 20 seconds at position 7, on ice (using a sonifier from Branson, Soest, The Netherlands). Precondensed Triton X-114 (Serva) in TBS was added to the sporozoite suspension to a final concentration of 10% (v/v) and mixed well to dissolve the proteins. Non-solubilised material was pelleted by centrifugation (20 min 12000 g at 4° C.). The supernatant recovered was layered over a 6% sucrose cushion and incubated 15 min 40° C. (phase separation) and spun 10 min 400 g at room temperature (RT). Extraction of the hydrophilic fraction was repeated once in 10% (v/v) and subsequently in 20% (v/v) precondensed Triton X-114. The total protein concentration was determined using the bichinchonic acid (BCA) assay (Pierce Chemicals, Rockford, Ill., USA). This hydrophilic phase was stored at −70° C. until further use.

Prep-Cell Fractionation

All procedures were performed at 4° C. Prior to fractionation, HPS was concentrated by acetone precipitation (HPS:acetone+1:9). After centrifugation for 60 min at 15000 g and 4° C. and air drying, pellets were dissolved in reducing sample buffer (Laemmli 1970) containing 30 mg/ml dithiotreitol (DTT) and boiled 3 min at 100° C. The hydrophilic proteins were fractionated using a 12% (w/v) poly acrylamide (PAA) separating gel (7 cm) and a 4% (w/v) PAA stacking gel in the 37 mm diameter tube of the Bio-Rad Prep-cell apparatus (Bio-Rad Labs, Richmond, Calif.) according to the manufacturer's protocol. The Prep-cell was operated at 40 mA, 500V max. Fractions (+3 ml) were collected overnight and stored at −85° C. Samples of the fractions were diluted once in 2× strength reducing sample buffer and analysed with sodium-dodecyl-sulphate polyacrylamide gel-electrophoresis (SDS-PAGE) using a 12% (w/v) PAA gel (Laemmli 1970). The gels were silverstained according to Wray et al. (Wray W., Boulikas T., Wray V. P. & Hannock R. (1981) Silver staining of proteins in polyacrylamide). Fifty fractions were analysed based on their relative molecular mass and dialysed against 0.01M phosphate buffered saline (PBS) pH 7.3. Those fractions containing proteins with a M.W. between 26 and 30 kD (+/−5 kD) were selected for further analysis.

The total protein concentration in the fractions was determined using the BCA assay.

Characterisation of Selected Antigens and Protein Sequencing.

Fractions containing polypeptides described under Prep-cell fractionation and ranging from 26-30 kD (±5 kDa, to allow for possible limitations in the measurement techniques used) were put on gel for further analysis.

They were further fractionated on a preparative 12% (w/v) polyacrylamide gel, stained with Coomassie Brilliant Blue and subsequently excised from the gel. Bands from these gels were used for sequencing purposes as described below:

The polypeptides in the gel slices were subjected to tryptic digestion as described by Rosenfeld et al., Anal. Biochem. 203: 173-179 (1992)

Thereafter, the tryptic digests were freed from the gel and pre-purified on preparative HPLC using the Trifluoracetic acid (TFA)-system, followed by preparative HPLC using the Ammonium Acetate system. The purified polypeptide fragments were sequenced using the standard Edman method as described (Edman, P., Acta Chem. Scand. 10: 761-768 (1956) and Ilse, D. & Edman, P., Aust. J. Chem. 16: 411-416 (1963)).

Example 2

Isolation/Cloning of DNA and DNA Sequencing

Cloning and sequencing of a fragment of the gene encoding the SOD-like 25 kD polypeptide.

mRNA was isolated from *E. tenella* first generation trophozoites (obtained from MDBK cells infected with freshly excysted sporozoites) at 40-48 hours after infection using Ultraspec total RNA isolation reagent (Biotecx Lab. inc., Houston, Tex.). 1st strand cDNA was synthesized using a SOD-specific backward primer, according to the ambiguity code GCRAARTCCCARTTIACIAC, which was deduced from a part (VVNWDFA) of oligopeptide YLDAWWSVVN-WDFANENLK which was isolated and sequenced as described above, and which is part of the sequence given in SEQ ID NO: 1. To the mRNA 0.5 µg primer was added and incubated at 70° C. for 10 min. The cDNA synthesis was performed using Superscript reverse transcriptase (cDNA synthesis kit, Gibco BRL). The reaction was incubated for 50 min at 41° C. The cDNA synthesis was stopped by rapid cooling on ice. Thereafter the cDNA was purified by phenol/chloroform extraction followed by precipitation in ethanol according to standard procedures (Sambrook T, et al). This specific primed cDNA was subjected to PCR using the backward primer and a specific forward primer, according to the ambiguity code (CCIGAYGCTYTIGARCCITAYAT), which was deduced from a part (PDALEPYI) of another oligopeptide, FSLPPLPYKPDALEPYIS, which was isolated and sequenced as described above, and which is also part of the sequence given in SEQ ID NO: 1. The reaction was run in a GeneAmp PCR system (Perkin Elmer) which was programmed as follows: 10 min 94° C.-1 min 94° C.; 30 sec 55° C.; 90 sec 68° C. (30 cycles)-10 min 68° C.; 4° C. The obtained PCR products were run on a 1% TAE agarose gel containing ethidium bromide. Specific PCR fragments were visualized using UV light and excised from the gel. The fragments were eluted from the gel by incubating the gel in an equal amount of deionized water overnight. The PCR fragments were cloned into a pCRII-topo blunt vector (Zero Blunt Topo PCR Cloning kit, Invitrogen, Leek, the Netherlands) according to the specifications of the manufacturer. Using pCRII-topo specific primers the inserted PCR fragment was sequenced using an ABI Prism 310 Genetic Analyzer (Perkin Elmer).

Cloning and sequencing of a fragment of the gene encoding the peroxidoxin-like 25 kD polypeptide.

The procedure was similar to the procedure described above, however the backward primer (TCIGTIGTRCAIACIGGIGTRAARTC) [SEQ. ID. NO.: 42] used for specific cDNA synthesis was deduced from a conserved part (DFTPVCTTE) of peroxidoxin molecules. In the PCR reaction this backward primer was used in combination with a forward primer (TTYCCIGAYTTYCARGCIGARGC) [SEQ. ID. NO.: 43] deduced from a part of the isolated oligopeptide (FPDFQAE).

Example 3

Vaccination Experiments

Determination of Vaccine Potential of Selected Polypeptides

Groups of chickens were immunised with the selected polypeptides. Animals received a priming vaccination at day 0 and a booster vaccination at day 21.

Fourteen days after booster vaccination all animals were challenged with E. tenella sporulated oocysts. Seven days later animals were sacrificed to determine the lesion score in the ceca. The group of animals vaccinated with the polypeptides according to the invention had reduced cecal lesion scores compared to non-vaccinated controls. This reduction was statistically significant ($P<0.05$).

Vaccination Experiments

The selected polypeptide volumes are pooled and adjusted to obtain 5-10 µg of a polypeptide according to the invention/dose (0.5 ml) unless otherwise indicated. To each dose 150 µg/dose Quill A (Superfos Biosector, Vedbaek, Denmark) is added as adjuvant. The different vaccine preparations are injected subcutaneously in groups of ±10 chickens. The control group is injected with adjuvant in PBS. After ±3 weeks chickens are boosted with the same preparation, which is prepared freshly from the frozen antigen stock.

The invention claimed is:

1. A vaccine for the protection of poultry against *Eimeria* infection, comprising the amino acid sequence as shown in SEQ ID NO.: 1, and a pharmaceutically acceptable carrier.

2. The vaccine according to claim 1, which additionally comprises an adjuvant.

3. The vaccine according to claim 1, which comprises at least one additional immunogen of a poultry pathogen.

4. The vaccine according to claim 3, wherein the at least one poultry pathogen is selected from the group consisting of Marek's Disease virus (MDV), Newcastle Disease virus (MDV), Infectious Bronchitis virus (IBV), Chicken Anaemia Agent (CAA), Reovirus, Avian Retrovirus, Fowl Adenovirus, Turkey Rhinotracheitis virus, *Salmonella* spp. and *E. coli*.

5. The vaccine according to claim 1 which is in freeze-dried form.

6. A method for the preparation of a vaccine for combatting *Eimeria* infections, comprising admixing the amino acid sequence as shown in SEQ ID NO.: 1 with a pharmaceutically acceptable carrier.

* * * * *